US009429562B2

(12) United States Patent
Schubert et al.

(10) Patent No.: US 9,429,562 B2
(45) Date of Patent: Aug. 30, 2016

(54) APPARATUS FOR DETERMINING AT LEAST ONE EVALUATION PARAMETER OF A BLOOD SAMPLE

(71) Applicant: C A CASYSO AG, Muttenz (CH)

(72) Inventors: Axel Schubert, Munich (DE); Kevin Bels, Munich (DE)

(73) Assignee: C A CASYSO AG, Muttenz (CH)

( * ) Notice: Subject to any disclaimer, the term of this patent is extended or adjusted under 35 U.S.C. 154(b) by 0 days.

(21) Appl. No.: 14/165,323

(22) Filed: Jan. 27, 2014

(65) Prior Publication Data

US 2014/0202231 A1   Jul. 24, 2014

Related U.S. Application Data

(62) Division of application No. 12/764,611, filed on Apr. 21, 2010, now Pat. No. 8,637,320.

(30) Foreign Application Priority Data

Mar. 24, 2010  (EP) .................................. 10157562

(51) Int. Cl.
*G01N 33/00* (2006.01)
*G01N 33/49* (2006.01)
*A61B 5/02* (2006.01)
*A61B 5/155* (2006.01)
(Continued)

(52) U.S. Cl.
CPC ........... *G01N 33/49* (2013.01); *A61B 5/02035* (2013.01); *A61B 5/1427* (2013.01); *A61B 5/14546* (2013.01); *A61B 5/155* (2013.01); *A61B 5/4821* (2013.01); *G06F 19/3431* (2013.01); *A61B 5/01* (2013.01); *A61B 5/14551* (2013.01); *A61B 5/153* (2013.01); *G01N 33/4905* (2013.01)

(58) Field of Classification Search
CPC .... G01N 33/49; G01N 33/4905; A61B 5/01; A61B 5/153
See application file for complete search history.

(56) References Cited

U.S. PATENT DOCUMENTS 3,714,815 A    2/1973   Hartert et al.
3,803,903 A    4/1974   Lin
(Continued)

FOREIGN PATENT DOCUMENTS

CN    101195112       6/2008
DE    27 40 932 A1    11/1978
(Continued)

OTHER PUBLICATIONS

Calatzis et al., "Strategies to Assess Individual Susceptibility to abciximab Therapy Using A New Functional Assay," Annals of Hematology, (Berlin, DE) vol. 76, No. Suppl 1, 1998, p. A61, XP009097526.
(Continued)

*Primary Examiner* — Sam P Siefke
(74) *Attorney, Agent, or Firm* — Jenkins, Wilson, Taylor & Hunt, P.A.

(57) ABSTRACT

The present invention provides a method for determining at least one evaluation parameter of a blood sample, comprising the following steps: providing (S4) at least one blood gas parameter; providing (S5) at least one hemostasis parameter; and determining (S6 . . . S10") the at least one evaluation parameter as a function of the blood gas parameter and/or the hemostasis parameter.

3 Claims, 5 Drawing Sheets

(51) Int. Cl.
*A61B 5/145* (2006.01)
*A61B 5/00* (2006.01)
*G06F 19/00* (2011.01)
*A61B 5/01* (2006.01)
*A61B 5/1455* (2006.01)
*A61B 5/153* (2006.01)

(56) References Cited

U.S. PATENT DOCUMENTS

| | | | |
|---|---|---|---|
| 4,148,216 | A | 4/1979 | Do et al. |
| 4,193,293 | A | 3/1980 | Cavallari |
| 4,319,194 | A | 3/1982 | Cardinal et al. |
| 4,726,220 | A | 2/1988 | Feier et al. |
| 4,765,180 | A | 8/1988 | Clifton |
| 4,767,600 | A | 8/1988 | Vicario |
| 5,164,598 | A | 11/1992 | Hillman et al. |
| 5,207,988 | A | 5/1993 | Lucas |
| 5,287,732 | A | 2/1994 | Sekiguchi |
| 5,447,440 | A | 9/1995 | Davis et al. |
| 5,531,102 | A | 7/1996 | Brookfield et al. |
| 5,777,212 | A | 7/1998 | Sekiguchi et al. |
| 5,777,215 | A | 7/1998 | Calatzis et al. |
| 5,902,937 | A | 5/1999 | Amrani et al. |
| 6,066,243 | A | 5/2000 | Anderson et al. |
| 6,200,532 | B1 | 3/2001 | Wu et al. |
| 6,537,819 | B2 | 3/2003 | Cohen et al. |
| 6,613,286 | B2 | 9/2003 | Braun et al. |
| 6,662,031 | B1 | 12/2003 | Khalil et al. |
| 6,699,718 | B1 | 3/2004 | Bruegger |
| 6,838,055 | B2 | 1/2005 | Sando et al. |
| 6,951,127 | B1 | 10/2005 | Bi |
| 7,399,637 | B2 | 7/2008 | Wright et al. |
| 7,412,877 | B1 | 8/2008 | Bi |
| 7,745,223 | B2 | 6/2010 | Schubert et al. |
| 8,110,392 | B2 | 2/2012 | Battrell et al. |
| 8,383,045 | B2 | 2/2013 | Schubert et al. |
| 8,448,499 | B2 | 5/2013 | Schubert et al. |
| 8,637,320 | B2 | 1/2014 | Schubert et al. |
| 8,857,244 | B2 | 10/2014 | Schubert et al. |
| 9,086,423 | B2 | 7/2015 | Schubert et al. |
| 9,110,084 | B2 | 8/2015 | Schubert et al. |
| 2002/0081741 | A1 | 6/2002 | Braun, Sr. |
| 2007/0059840 | A1 | 3/2007 | Cohen et al. |
| 2009/0130645 | A1 | 5/2009 | Schubert et al. |
| 2010/0154520 | A1 | 6/2010 | Schubert et al. |
| 2010/0184201 | A1 | 7/2010 | Schubert et al. |
| 2011/0237913 | A1 | 9/2011 | Schubert et al. |
| 2013/0323846 | A1 | 12/2013 | Schubert et al. |
| 2013/0323847 | A1 | 12/2013 | Schubert et al. |
| 2013/0323848 | A1 | 12/2013 | Schubert et al. |
| 2013/0333448 | A1 | 12/2013 | Schubert et al. |

FOREIGN PATENT DOCUMENTS

| | | |
|---|---|---|
| DE | 10135569 | 2/2003 |
| EP | 0404456 A | 12/1990 |
| EP | 1367392 | 12/2003 |
| EP | 1627725 A2 | 2/2006 |
| EP | 1884778 | 2/2008 |
| EP | 2371284 | 10/2011 |
| GB | 2257256 A | 1/1993 |
| WO | WO 02/063273 | 8/2002 |
| WO | WO2005/106467 | 11/2005 |
| WO | WO 2006/091650 | 2/2006 |
| WO | WO 2006/126290 | 11/2006 |
| WO | WO2008/093216 | 8/2008 |
| WO | WO2011/117017 | 2/2011 |

OTHER PUBLICATIONS

Chakroun et al., "The influence of Fibrin Polymerizatino and Platelet-Mediated Contractile Forces on Citrated Whole Blood Thromboelstography Profile," Thrombosis and Haemostasis, May 2006, vol. 95, No. 5, pp. 822-828.

Hartert H: "Blood Coagulation Studies with Thromboelastography—A New Research Method," Klin Wochenschrift, 26:577-583, 1948—English translation.

Kawasaki et al., "The Effects of Vasoactive Agents, Platelet Agonists and Anticoagulation on Thrombelastography," Acta Anaesthesiologica Scandinavica, Oct. 2007, vol. 51, No. 9, pp. 1237-1244.

Nield et al., "MRI-Based Blood Oxygen saturation measurements in infants and children with congenital heart disease," Pediatric Radiology (2002) 32:518-522.

Noon et al., "Reduction of Blood Trauma in Roller Pumps for Long-term Perfusion" World J. Surg. (9), 1985, pp. 65-71.

Novotny et al., "Platelets Secrete a Coagulation Inhibitor . . . ", Blood 1988 (72), pp. 2020-2025.

Rodzynek et al., "The Transfer Test: A New Screening Procedure for Thrombotic Diseases," The Journal of Surgical Research, Sep. 1983, vol. 35, No. 3, pp. 227-233.

Rotem Brochure—"When Minutes Count to Stop the Bleeding," Pentapharm GmbH, www.rotem.de, Jun. 2007.

Rugeri et al., "Diagnosis of Early Coagulation Abnormalities in Trauma Patients by Rotation Thrombelastography," Journal of Thrombosis and Haemostasis, Feb. 2007, vol. 5, No. 2, pp. 289-295.

Salooja et al., "Thrombelastography," Blood Coagulation & Fibrinolysis, vol. 12, No. 5, 2001, pp. 327-337.

Shore-Lesserson et al., "Thromboelastography-guided transfusion algorithm reduces tranfusions in complex cardiac surgery," Anesthesia and Analgesia, Feb. 1999, vol. 88, No. 2, pp. 312-319.

Soria et al., "Fibrin Stabilizing Factor (F XIII) and Collagen Polymerization", Path. Biol. Suppl. 22 (86), 1974, pp. 1355-1357.

Spannagl et al., "Point-of-Care Analysis of the Homostatic System," Laboratoriumsmedizin, (Kirchheim, DE), vol. 26, No. 1-2, Feb. 2002, pp. 68-76.

Srinivasa et al., "Thromboelastography: Where Is It and Where Is It Heading?" Int'l Anesthesiology Clinics, vol. 39, Iss. 1, Winter 2001, pp. 35-49.

Tanaka et al., "Thrombin Generation Assay and Viscoelastic Coagulation . . . " Anesthesia & Analgesia vol. 105, No. 4, Oct. 2007.

European Search Report for EP 07121222 dated Apr. 9, 2008.

European Search Report for EP 08172769 dated Jun. 4, 2009.

European Search Report for EP 09150740 dated Jun. 30, 2009.

International Search Report and Written Opinion for PCT/EP2010/050454 dated Apr. 20, 2010.

Office Action with Restriction/Election Requirement for U.S. Appl. No. 12/275,757 dated Sep. 15, 2010.

Non-Final Office Action for U.S. Appl. No. 12/275,757 dated Jan. 21, 2011.

Non-Final Office Action for U.S. Appl. No. 12/275,757 dated Oct. 18, 2011.

Non-Final Office Action for U.S. Appl. No. 12/688,306 dated Nov. 9, 2011.

Interview Summary for U.S. Appl. No. 12/275,757 dated Dec. 12, 2011.

Final Office Action for U.S. Appl. No. 12/688,306 dated Apr. 24, 2012.

Notice of Abandonment (per client) for U.S. Appl. No. 12/275,757 dated May 8, 2012.

Notice of Allowance for U.S. Appl. No. 12/688,306 dated Jul. 26, 2012.

Non-Final Office Action for U.S. Appl. No. 12/640,376 dated Aug. 15, 2012.

International Preliminary Report and Written Opinion for PCT/EP2011/051803 dated Sep. 25, 2012.

Notice of Allowance for U.S. Appl. No. 12/688,306 dated Nov. 1, 2012.

Notice of Allowance for U.S. Appl. No. 12/640,376 dated Jan. 29, 2013.

Non-Final Office Action for U.S. Appl. No. 12/764,611 dated Feb. 13, 2013.

Supplemental Notice of Allowance for U.S. Appl. No. 12/640,376 dated Feb. 28, 2013.

Chinese Office Action for Application No. 200980151858.5 dated Apr. 15, 2013.

(56) References Cited

OTHER PUBLICATIONS

Notice of Allowance for U.S. Appl. No. 12/764,611 dated Aug. 16, 2013.

Non-Final Office Action for U.S. Appl. No. 13/895,002 dated Dec. 20, 2013.

Final Office Action for U.S. Appl. No. 13/895,002 dated Apr. 11, 2014.

Notice of Allowance for U.S. Appl. No. 13/895,002 dated Aug. 26, 2014.

Non-Final Office Action for U.S. Appl. No. 13/895,053 dated Dec. 10, 2014.

Notice of Allowance for U.S. Appl. No. 13/395,053 dated Mar. 31, 2015.

Notice of Allowance for U.S. Appl. No. 13/894,998 dated Apr. 13, 2015.

Non-Final Office Action for U.S. Appl. No. 13/895,034 dated Jul. 14, 2015.

Notice of Allowance for U.S. Appl. No. 13/895,034 dated Nov. 5, 2015.

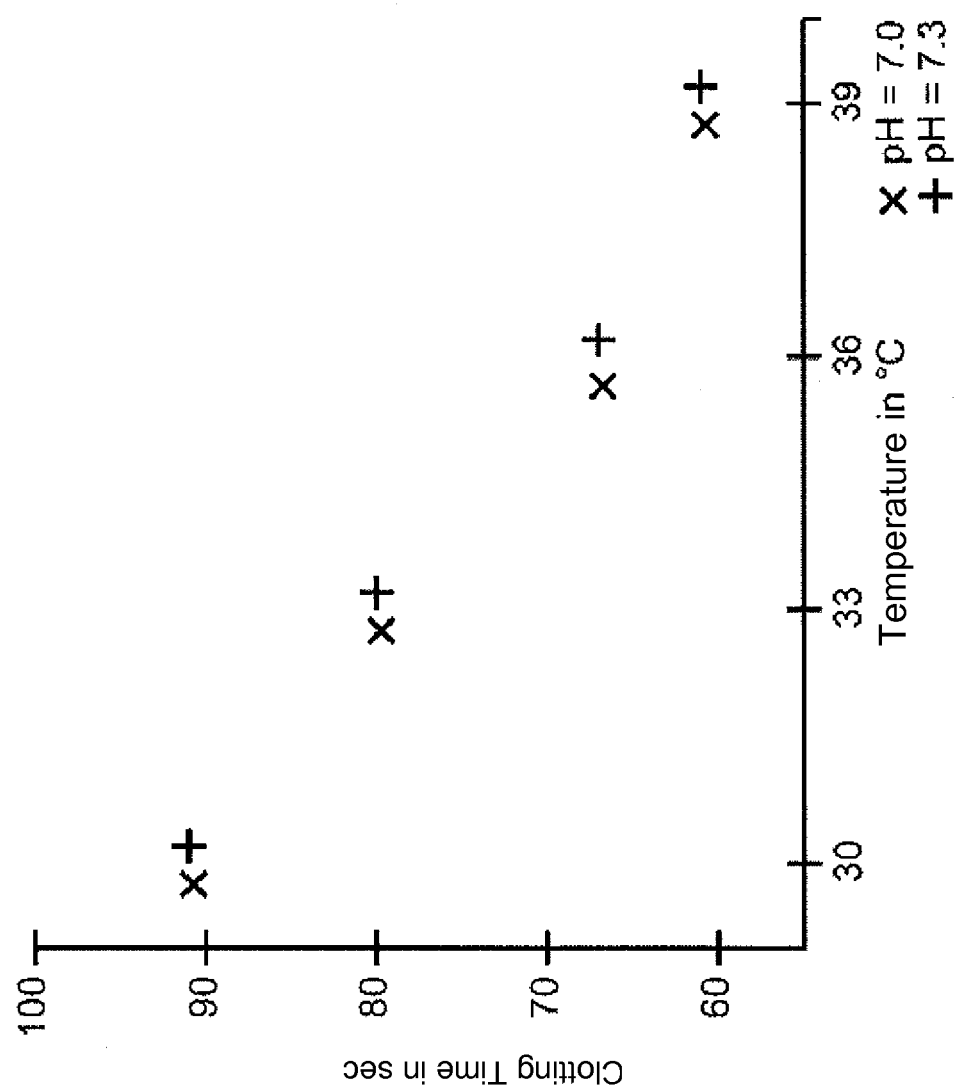

APPARATUS FOR DETERMINING AT LEAST ONE EVALUATION PARAMETER OF A BLOOD SAMPLE

CROSS-REFERENCE TO RELATED APPLICATIONS

This application is a divisional of and claims priority to U.S. patent application Ser. No. 12/764,611 filed Apr. 21, 2010, which claims the benefit of European patent application No. 10 157 562.9 filed Mar. 24, 2010, the entire disclosures of which are herein incorporated by reference.

FIELD OF THE INVENTION

The present invention relates to a method and apparatus for determining at least one evaluation parameter of a blood sample.

BACKGROUND OF THE INVENTION

During the perioperative period, the anesthetist has to monitor, control and interpret a great number of factors having an influence on the patient's well being. These factors are, in particular, hemostasis, oxygenation, nutrition, ph-level and body temperature. Further, the anesthetist must evaluate the influence of a blood product being transfused to a patient who has suffered a severe loss of blood.

Hemostasis is the process by which bleeding from a damaged blood vessel stops. It is a dynamic, extremely complex process involving many interacting factors, which include coagulation, i.e. the process by which blood clots are formed, fibrinolytic proteins, activators, inhibitors and cellular elements. Since none of these factors remains static or works in isolation, it is necessary to measure continuously all phases of a patient's hemostasis as a net product of all blood components in a non-isolated and non-static fashion.

Furthermore, it is well known that coagulopathy is sometimes confused with hypothermia, acidosis and preexisting disorders like morbid ionized calcium concentration. For example:

Trauma patients are prone to hypothermia, which slows down enzymatic reactions, modifies platelet function, decreases platelet counts and stimulates fibrinolysis.

Acidosis worsens fibrin polymerization and strengthening of the clot.

Low ionizied calcium concentration (as the result of a massive PRBC transfusions containing citrate) and a low hematocrit (<30%) further aggravate bleeding diathesis.

Increased base deficit (BD) or decreased base excess (BE), respectively, are known to influence the haemostatic potential.

Various methods have been introduced to assess hemostasis parameters like the potential of blood to form an adequate clot. Common laboratory tests such as thrombocyte counts or the determination of fibrin concentration provide information on whether the tested component is available in sufficient amount but lack in answering the question whether the tested component works properly under physiological conditions (e.g. the activity of fibrinogen under physiological conditions cannot be accessed by common optical methods).

A group of tests which overcomes these problems is summarized by the term "viscoelastic methods". The common feature of these methods is that the blood clot firmness (or other parameters dependent thereon) is continuously determined, from the formation of the first fibrin fibres until the dissolution of the blood clot by fibrinolysis. Blood clot firmness is a functional parameter, which is important for hemostasis in vivo, as a clot must resist blood pressure and shear stress at the site of vascular injury. Clot firmness results from multiple interlinked processes: coagulation activation, thrombin formation, fibrin formation and polymerization, platelet activation and fibrin-platelet interaction and can be compromised by fibrinolysis. Thus, by the use of viscoelastic monitoring all these mechanisms of the coagulation system can be assessed.

The first viscoelastic method was called "thromboelastography" (Hartert H: Blutgerinnungsstudien mit der Thromboelastographie, einem neuen Untersuchungsverfahren. Klin Wochenschrift 26:577-583, 1948). In the thromboelastography, the sample is placed in a cup that is periodically rotated to the left and to the right by about 5°, respectively. A pin is freely suspended by a torsion wire. When a clot is formed it starts to transfer the movement of the cup to the pin against the reverse momentum of the torsion wire. The movement of the pin as a measure for the clot firmness is continuously recorded and plotted against time. For historical reasons the firmness is measured in millimeters.

One of the most important parameters determined by thromboelastography is the time between the activator induced start of the coagulation cascade and the time until the first long fibrin fibres have been built up which is indicated by the firmness signal exceeding a defined value. This parameter will be called clotting time in the following. Another important parameter is the clot formation time which gives a measure for the velocity of the development of a clot. The clot formation time is defined as the time it takes for the clot firmness to increase from 2 to 20 mm. The maximum firmness a clot reaches during a measurement, further on referred to as maximum clot firmness or just MCF, is also of great diagnostic importance.

Modifications of the original thromboelastography technique (Hartert et al. (U.S. Pat. No. 3,714,815) have been described by Cavallari et al. (U.S. Pat. No. 4,193,293), by Do et al. (U.S. Pat. No. 4,148,216), by Cohen (U.S. Pat. No. 6,537,819), further modifications by Calatzis et al. (U.S. Pat. No. 5,777,215) are called thromboelastometry.

Besides hemostasis, parameters like oxygenation, nutrition and ph-level need to be analyzed by the anesthetist. It is commonly known to use blood gas analyzers as described in EP 1 367 392 A1 for this purpose. Blood gas analyzers generally measure the partial pressures of certain gases in a blood sample and other parameters like ph-level and hematocrit. From these partial pressures oxygenation and other factors can be deduced. Devices known as clinical chemistry analyzers are also available in the market. These devices are also used to determine some of the parameters determined by blood gas analyzers. When it is referred to blood gas analyzers henceforth, this is also to include clinical chemistry analyzers and electrolyte analyzers. Further, when it is referred to blood gas parameters henceforth, this is also to include clinical chemistry parameters and electrolyte parameters.

Further, in current practice blood products are usually prepared and applied according to fixed protocols independently from any individual properties of the initial donor or other influences (e.g., storage duration, storage conditions, etc.). In particular, their potential to interact with other factors like the patient's oxygenation, ph-level or hemostasis are not assessed prior to application of the blood products nowadays.

Monitoring, controlling and interpreting this great number of factors as well as their interdependence, especially in stressful environments like operation theaters, put great pressure on the anesthetist. This pressure may result in mistakes with severe consequences for the patient.

It is therefore an object of the present invention to support the anesthetist and/or provide the anesthetist with information in a better way.

SUMMARY OF THE INVENTION

Accordingly, a method for determining at least one evaluation parameter of a blood sample is provided, the method comprising the following steps: providing at least one blood gas parameter; providing at least one hemostasis parameter; and determining the at least one evaluation parameter as a function of the blood gas parameter and the hemostasis parameter.

Furthermore, an apparatus for determining at least one evaluation parameter of a blood sample is provided, in particular for performing the method according to the invention, the apparatus comprising: a blood gas unit for providing at least one blood gas parameter; a hemostasis unit for providing at least one hemostasis parameter; and a evaluation unit for determining the at least one evaluation parameter as a function of the blood gas parameter and the hemostasis parameter.

Furthermore, a computer program being adapted to perform the method according to the invention on a computer is provided.

Furthermore, a data carrier which stores a computer program according to the invention is provided.

The at least one evaluation parameter that is determined as a function of the blood gas parameter and the hemostasis parameter can be provided to the anesthetist in one or another way to simplify his decision making process, or even obviate the same. Alternatively or additionally, the evaluation parameter can be used to verify the anesthetist's decision making process, thus making it more safe. Of course, the evaluation parameter may also be provided to another device that performs a function related to anesthetics, for example. Such a device may be a cardiopulmonary bypass device.

Preferred embodiments are given in the dependent claims.

Herein, a "blood sample" refers to a whole blood sample and/or a sample containing blood components, e.g. a blood plasma sample.

According to a preferred embodiment of the method of the present invention the step of providing the blood gas parameter comprises at least one of the following steps: performing a blood gas analysis, measuring the blood gas parameter, reading out a sensor, reading out a data input device and/or reading out a data storage. The blood gas analysis may be preformed using a blood gas analyzer as described above. The sensor may be a keyboard, for example, that the anesthetist uses to enter the blood gas parameter.

According to a further preferred embodiment of the method of the present invention the blood gas parameter is selected from and/or is a function of at least one of a group of parameters, the group comprising: a partial pressure of carbon dioxide, a partial pressure of oxygen, a partial pressure of nitrogen oxide, a pH-level, a base excess, a base deficit, hematocrit, a bicarbonate level, a concentration of lactate, a concentration of electrolytes, in particular calcium ions, a concentration of hemoglobin, a concentration of oxyhemoglobin, a concentration of carboxyhemoglobin and/or a concentration of methemoglobin.

According to a further preferred embodiment of the method of the present invention the step of providing the hemostasis parameter comprises at least a one of the following steps: performing a hemostasis analysis, measuring the hemostasis parameter, reading out a sensor, reading out a data input device and/or reading out a data storage. The hemostasis analysis may be preformed using any one of the methods as described above, for example a viscoelastic method, in particular thromboelastography. Traditional methods like thrombocyte count may also be used. The sensor may be a keyboard, for example, that the anesthetist uses to enter the hemostasis parameter. The data storage may be part of the evaluation unit for determining the at least one evaluation parameter as a function of the blood gas parameter and the hemostasis parameter or it may be part of the hemostasis unit, e.g. a thromboelastometer.

According to a further preferred embodiment of the method of the present invention the hemostasis parameter is a coagulation parameter or a clot lysis parameter. Whereas hemostasis describes the entire process by which bleeding from a damaged blood vessel stops, coagulation only refers to the process of forming blood clots. "Lysis" refers to the process by which a blood clot is dissolved, i.e. the opposite of coagulation. Lysis is basically initiated by the activity of plasmin. An example for a clot lysis parameter is the decrease in clot firmness in relation to the maximum clot firmness or the plasmin level.

According to a further preferred embodiment of the method of the present invention the coagulation parameter is selected from and/or is a function of at least one of a group of parameters, the group comprising: a clotting time, a clot formation time, a clot firmness, a maximum clot firmness, a fibrinogen functionality, a platelet functionality, an inhibitor functionality, in particular a protein C-level, a tissue factor passway inhibitor (TFPI)-level or an ATIII-level, and/or sample viscosity. An example for a fibrinogen functionality is the clot firmness or maximum clot firmness of a viscoelastic measurement of a blood sample in the presence of a platelet inhibitor. An example for a platelet functionality is the difference of the clot firmnesses or maximum clot firmnesses of a viscoelastic measurement of a blood sample in the absence and in the presence of a platelet inhibitor. Another example of the platelet functionality is the aggregation behavior of the blood sample in the presence of a platelet activator, e.g. measured by optical or electrical means.

According to a further preferred embodiment of the method of the present invention it comprises the steps of: providing a temperature parameter of the blood sample, a temperature parameter of a patient's body and/or an expected temperature parameter of a patient's body and determining the evaluation parameter also as a function of the temperature parameter and/or expected temperature parameter. When it is referred to a temperature parameter henceforth, this is also to include an expected temperature parameter, preferably. For example, patients are typically cooled down during heart operations. The temperature of the blood sample taken from such a patient may be much lower than normal having a direct influence on blood gas analysis as well as hemostasis analysis. For example, the low temperature will result in a high oxygen saturation of the blood sample, thereby changing the partial pressure of oxygen, i.e. a typical blood gas parameter, measured in blood gas analysis. Further, the low temperature may result in significantly prolonged clotting times. By taking the patient's expected temperature into account blood gas parameters and/or hemostasis parameters can be corrected accordingly in order to properly assess the patient's condition when he is at the expected temperature, e.g. just before he wakes up from anesthesia. On the other hand, the blood sample, being cool initially, warms up until blood gas analysis as well as hemostasis analysis is completed. Again, by taking the patient's temperature into account, blood gas parameters and/or hemostasis parameters can be corrected to the patient's actual temperature in order to correctly assess hemostasis at the patient's actual temperature.

According to a further preferred embodiment of the method of the present invention the step of providing the temperature parameter comprises at least a one of the following steps: measuring the temperature parameter, reading out a sensor, reading out a data input device and/or reading out a data storage. A thermometer connected to the patient is one example of a suitable sensor. The input device may be a keyboard, for example, used by the anesthetist to enter the patient's temperature manually.

According to a further preferred embodiment of the method of the present invention the step of determining the evaluation parameter comprises at least one of the following steps: comparing the blood gas parameter with a blood gas parameter range and/or comparing the blood gas parameter with a blood gas parameter value. These blood gas parameter ranges or values are typically determined up front or can be found in the relevant literature and may be provided in the form of tables in electronic format to carry out the step of comparing. By way of this comparison, it can, for example, be determined if a blood gas parameter is inside an allowable range which will ensure that the hemostasis parameters obtained are meaningful.

According to a further preferred embodiment of the method of the present invention the step of determining the evaluation parameter comprises at least one of the following steps: comparing the temperature parameter with a temperature parameter range and/or comparing the temperature parameter with a temperature parameter value. These temperature parameter ranges or values (which may include expected temperature ranges or values) are typically determined up front or can be found in the relevant literature and may be provided in the form of tables in electronic format to carry out the step of comparing. By way of this comparison, it can, for example, be determined if the temperature parameter is inside an allowable range which will ensure that the hemostasis parameters obtained are meaningful.

According to a further preferred embodiment of the method of the present invention it further comprises the step of providing an interdependence parameter describing an interdependence between at least two of a group of parameters, the group comprising: the blood gas parameter, the hemostasis parameter and the temperature parameter. As outlined above some blood gas parameters and/or hemostasis parameters are dependent on temperature. However, others are not, or not to a relevant extent. The interdependence parameter may only describe if there is a dependence or not. However, the interdependence may also describe the degree of dependence. These dependence parameters are typically determined up front or can be found in the relevant literature and may be provided in the form of tables in electronic format to carry out the step of providing.

According to a further preferred embodiment of the method of the present invention the blood gas parameter range, the blood gas parameter value, the temperature parameter range, the temperature parameter value and/or the interdependence parameter is provided by means of calculating, estimating, measuring, reading out a sensor, reading out a data input device and/or reading out a data storage.

According to a further preferred embodiment of the method of the present invention the step of comparing the blood gas parameter with a blood gas parameter range and/or comparing the blood gas parameter with a blood gas parameter value is performed as a function of the interdependence parameter. For example, if according to an interdependence parameter a specific hemostasis parameter, for example the clotting time, is dependent on a blood gas parameter, for example pH-value, then only will the blood gas parameter be compared to the blood gas parameter range or value. Otherwise, this comparison shall not be carried out to ensure an efficient process.

According to a further preferred embodiment of the method of the present invention the step of comparing the temperature parameter with a temperature parameter range and/or comparing the temperature parameter with a temperature parameter value is performed as a function of the interdependence parameter. For example, if according to an interdependence parameter a specific hemostasis parameter, for example the clotting time, is dependent on a temperature parameter, for example the temperature of the blood sample, then only will the temperature parameter be compared to the temperature parameter range or value. Otherwise, this comparison shall not be carried out to ensure an efficient process.

According to a further preferred embodiment of the method of the present invention the hemostasis parameter is corrected as a function of the blood gas parameter and/or temperature parameter. For example, if a blood gas parameter and/or temperature parameter is not within its allowable range, the hemostasis can be corrected accordingly. Hence, adjusting of the blood gas parameter and/or temperature parameter up front, e.g. by chemical/biological means, can be avoided, thus ensuring an efficient process.

According to a further preferred embodiment of the method of the present invention the blood gas parameter is corrected as a function of the hemostasis parameter and/or temperature parameter. It is preferred to adapt the hemostasis parameter as a function of the blood gas parameter. However, in some instances it may be preferable to do it the other way around. Possibly, the hemostasis parameter and the blood gas parameter both depend on temperature which may require adapting both parameters.

According to a further preferred embodiment of the method of the present invention the hemostasis parameter, corrected hemostasis parameter, blood gas parameter and/or corrected blood gas parameter is transmitted to a data output device and/or output by a data output device as a function of the determined evaluation parameter. For example, if it is indicated by the interdependence parameter that the hemostasis parameter is not dependent on the blood gas parameter, then the evaluation parameter is set to equal 1 (Boolean). When the evaluation parameter equals 1, then the hemostasis parameter is displayed on an output device, e.g. a computer screen, to the anesthetist. Otherwise, if the interdependence parameter shows that the hemostasis parameter is dependent on the blood gas parameter and it is found that the blood gas parameter is out of its allowable range, then the evaluation parameter is set to 0. When the evaluation parameter equals 0, then the hemostasis value is not displayed on the output device.

According to a further preferred embodiment of the method of the present invention the evaluation parameter is transmitted to a data output device and/or output by a data output device. By another example, if the interdependence parameter shows that the hemostasis parameter is dependent on the blood gas parameter and it is found that the blood gas parameter is out of its allowable range, then the hemostasis value is displayed on the output device; however, the evaluation parameter is set to the message "Blood gas parameter out of range" which is displayed on the screen.

According to a further preferred embodiment of the method of the present invention an output information and/or a control command for the data output device is selected from a plurality of output information and/or control commands as a function of the determined evaluation parameter. By another example, if the interdependence parameter shows that the hemostasis parameter is dependent on the blood gas parameter and it is found that the blood gas parameter is out of its allowable range, then the hemostasis value is displayed on the output device. The evaluation parameter may depend on the specific type of blood gas parameter being out of range. Then, depending on the evaluation parameter an output information, e.g. a message saying "pH-level out of range", is selected from a plurality of output information, e.g. a table of messages "pH-level out of range", "partial pressure of oxygen out of range" etc. and displayed on the screen along with the hemostasis parameter.

According to a further preferred embodiment of the method of the present invention the steps of providing the blood gas parameter and the hemostasis parameter comprise the step of analyzing the same sample or different samples of blood. Analyzing only one sample can be more efficient though.

According to a further preferred embodiment of the method of the present invention the step of analyzing the same sample of blood comprises the step of proving the same sample or different samples of blood without additives. For example, when the period of time between taking the blood sample of the patient and performing the blood gas analysis and/or the hemostasis is small it may be advantageous to not add any additives because the time for substantial coagulation to take place is small. Without additives being added to the blood more accurate measurements of the blood gas parameter and/or the hemostasis parameter may be possible.

According to a further preferred embodiment of the method of the present invention the step of analyzing the same sample or different samples of blood comprises the step of adding inhibitors and/or antagonists. The inhibitor, e.g. heparin, may be required to prevent coagulation whilst measuring the blood gas parameter, e.g. pH-level. Thereafter, when measuring the hemostasis parameter, e.g. clot firmness, in the same blood sample, heparin may be detrimental. Therefore, an antagonist is added, e.g. protamin, which will allow the blood to clot again.

According to a further preferred embodiment of the method of the present invention the blood sample is taken from the patient at the point of care or from a blood product. Herein, a blood product means whole blood or any component, e.g. red blood cells, blood plasma, or platelets, of blood which is collected from a donor for use in a blood transfusion.

According to a further preferred embodiment of the method of the present invention a blood sampling time, blood sample identifier and/or patient identifier is assigned to the blood gas parameter, hemostasis parameter, temperature parameter and/or evaluation parameter. For example, the blood gas parameter, the blood sampling time, i.e. the point in time that the blood sample was taken, and the blood sample identifier, i.e. a unique code which is, e.g., associated with the patient or blood product, is electronically stored together in the same matrix together with the blood gas parameter, hemostasis parameter, temperature parameter and/or evaluation parameter.

According to a further preferred embodiment of the apparatus of the present invention it further comprises a temperature unit for providing a temperature parameter of the blood sample, a temperature parameter of a patient's body and/or an expected temperature parameter of a patient's body, wherein the evaluation unit determines the evaluation parameter also as a function of the temperature parameter and/or expected temperature parameter. Providing and using a temperature parameter in determining the evaluation parameter may be advantageous as already outlined above.

According to a further preferred embodiment of the apparatus of the present invention at least one the blood gas unit, hemostasis unit, evaluation unit and/or temperature unit is selected from a group, the group comprising: a technical device, a computer system, a server, a client and a mobile device.

Typically, the blood gas unit is a blood gas analyzer.

Typically, the hemostasis unit is a hemostasis analyzer, in particular a rheometric or viscoelastic measurement unit. An example for a viscoelastic measurement unit is a thromboelastometer or a thrombelastograph.

Typically, the temperature unit is a thermometer, in particular a thermometer in direct contact with the patient or a remotely sensing thermometer.

According to a further preferred embodiment of the apparatus of the present invention the blood gas unit, the hemostasis unit, the evaluation unit and/or the temperature unit are integrated into a single housing. This may be space and resource efficient.

According to a further preferred embodiment of the apparatus of the present invention it has a single cartridge for receiving the blood sample. Thus, the same blood sample is used for measuring the blood gas parameter, hemostasis parameter and/or temperature parameter.

According to a further preferred embodiment of the apparatus of the present invention it has a single cartridge for receiving two different blood samples. Thus, two different blood samples are used for measuring the blood gas parameter, hemostasis parameter and/or temperature parameter. The two samples may differ with respect to the additives in each blood sample, e.g. different coagulation inhibitors may have been added to the two blood samples.

According to a further preferred embodiment of the apparatus of the present invention a temperature of the blood gas unit and/or the hemostasis unit is controlled as a function of the temperature parameter. For example, it may be useful for the blood gas unit and/or the hemostasis unit to be at the patient's temperature thus allowing to properly assess the patient's actual condition.

BRIEF DESCRIPTION OF THE DRAWINGS

Other objects, features and advantages of the present invention will become apparent from the subsequent description and the appended claims, taken in conjunction with the accompanying drawings, in which:

FIG. 5 is a diagram showing clotting time vs. temperature for two different pH levels;

DETAILED DESCRIPTION OF PREFERRED EMBODIMENTS

Figure 1:
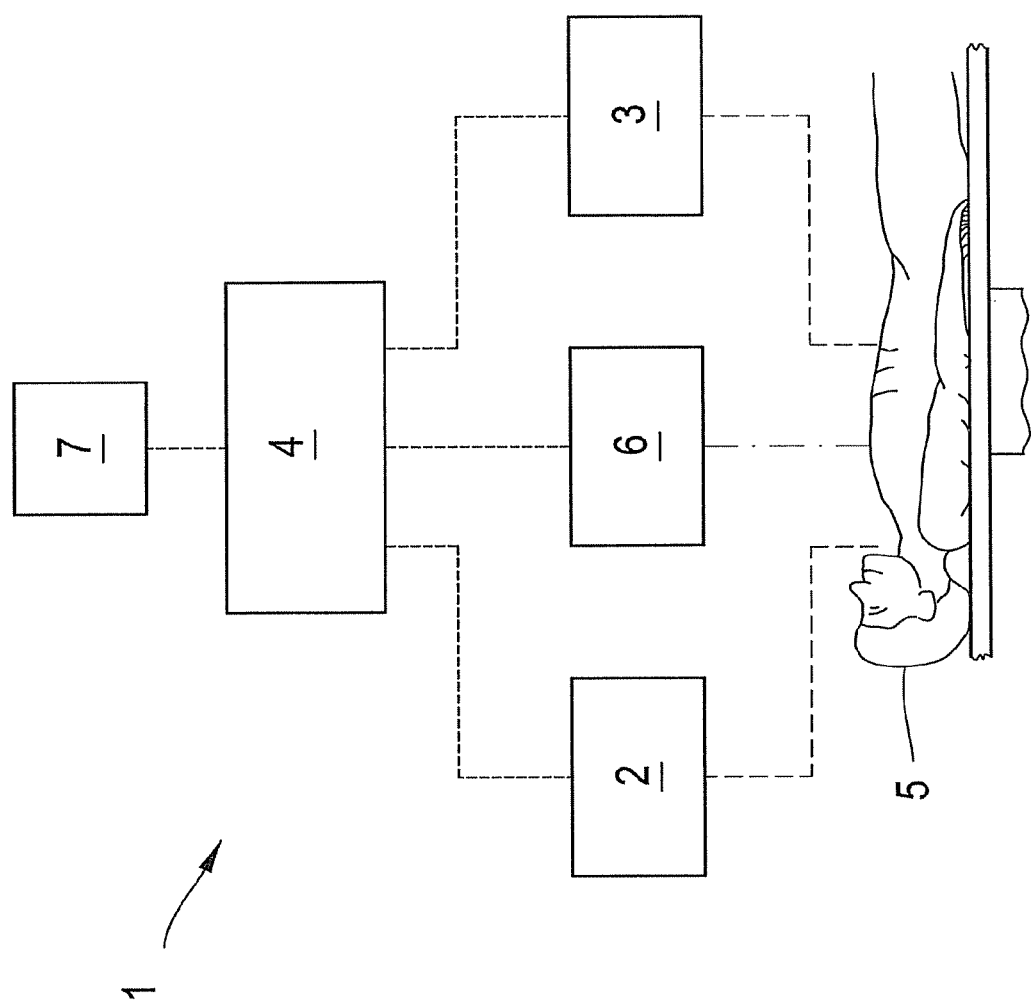
FIG. 1 is a schematic diagram of a preferred embodiment of an apparatus in accordance with the present invention.

In the figures like reference numerals designate like or functionally equivalent elements unless otherwise indicated.

FIG. 1 shows an apparatus 1 having an hemostasis unit 2, a blood gas unit 3 and an evaluation unit 4.

The hemostasis unit 2 provides an hemostasis parameter to the evaluation unit 4 as indicated by the dotted line in FIG. 1. The hemostasis unit 2 is formed as a thromboelastometer, for example as described in U.S. Pat. No. 5,777,215. Typical hemostasis parameters that may be determined using the thromboelastometer 2 are clotting time and clot formation time as defined in the introduction. To this end, a blood sample is taken from a patient 5—as indicated by the dashed line in FIG. 1—and analyzed in the thromboelastometer 2. The thromboelastometer 2 has a data interface by which the hemostasis parameter can be transmitted to the evaluation unit 4.

As an alternative, the hemostasis unit 2 may be formed as a keyboard for the anesthetist to enter the hemostasis parameter manually.

The blood gas unit 3 provides a blood gas parameter to the evaluation unit 4 as indicated by the dotted line in FIG. 1. The blood gas unit 3 is formed as a blood gas analyzer, for example as described in EP 1 367 392 A1. Typical blood gas parameters that may be determined using the blood gas analyzer 3 are pH-level and the partial pressure of oxygen. To this end, another blood sample is taken from the patient 5—as indicated by the dashed line in FIG. 1—and analyzed in the blood gas analyzer 3. The blood gas analyzer 3 has a data interface by which the blood gas parameter can be transmitted to the evaluation unit 4.

As an alternative, the blood gas unit 3 may be formed as a keyboard for the anesthetist to enter the blood gas parameter manually.

The evaluation unit determines at least one evaluation parameter as a function of the blood gas parameter and the hemostasis parameter. The evaluation parameter will support the anesthetist in his diagnosis of the patient's condition as explained in more detail with reference to FIG. 3. This support may lie in reducing the complexity of the data the anesthetist has to deal with. Additionally or alternatively, the evaluation parameter may be used to verify data and/or the anesthetist's decision making process. The evaluation unit is formed as a computer.

The blood sample may also be taken from a blood product to be transfused to the patient 5.

The apparatus 1 may further comprise a temperature unit 6. The temperature unit 6 provides a temperature parameter to the evaluation unit 4 as indicated by the dotted line in FIG. 1.

The temperature unit 6 is formed as a thermometer measuring—as indicated by the dashed-and-dotted line—the temperature parameter, for example the patient's temperature. The thermometer 6 has a data interface by which the temperature parameter can be transmitted to the evaluation unit 4. The evaluation unit 4 determines the evaluation parameter also as a function of the temperature parameter.

As an alternative, the temperature unit 6 may be formed as a keyboard for the anesthetist to enter the temperature parameter manually. This may be the patient's actual temperature or his expected temperature, for example.

Of course, numerous arrangements are conceivable: for instance, the evaluation unit 4 may be physically integrated into the hemostasis unit 2 or the blood gas analyzer 3.

The apparatus 1 may further include an output device 7, e.g. a screen, for displaying the evaluation parameter to the anesthetist. To this end, the screen 7 has a data interface to the evaluation unit 4 indicated by the dotted line in FIG. 1.

Figure 2:
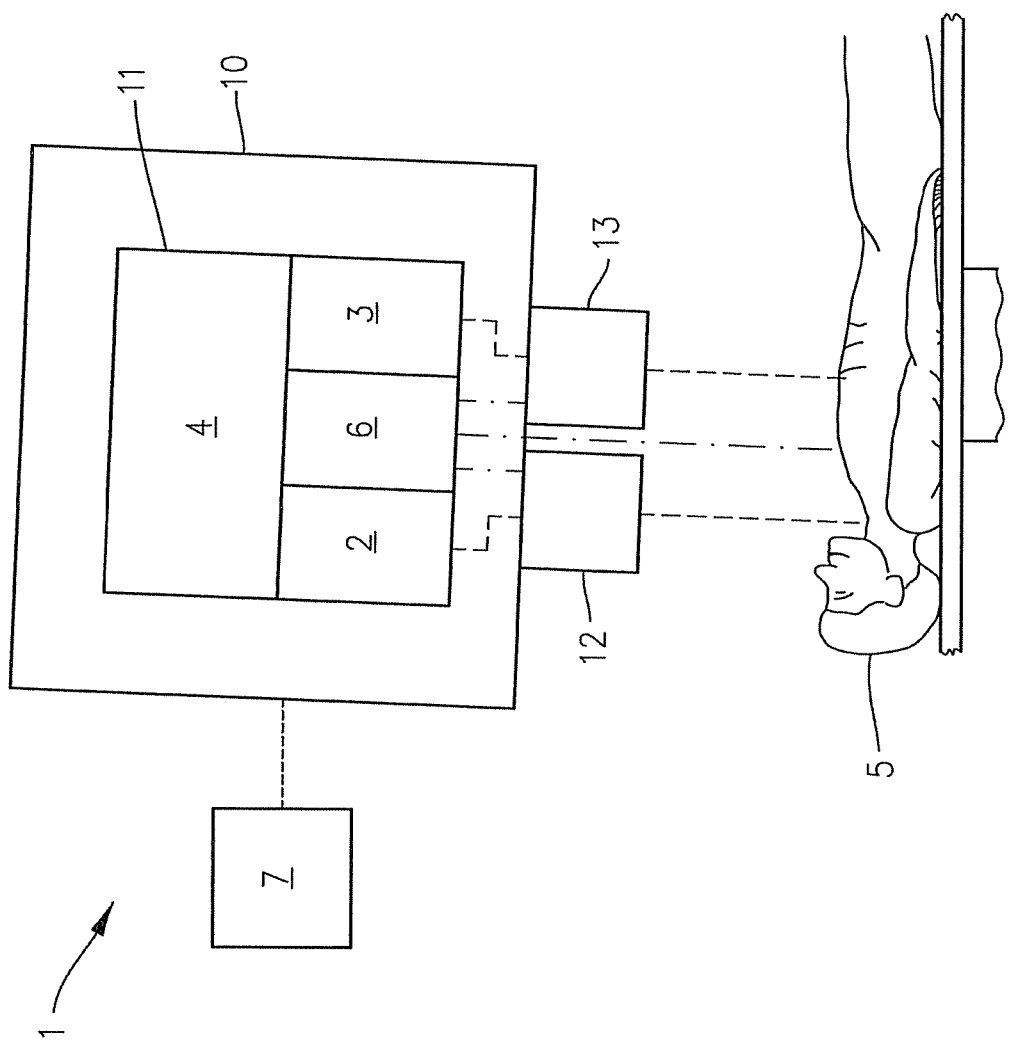
FIG. 2 is a schematic diagram of another preferred embodiment of an apparatus in accordance with the present invention.

FIG. 2 shows the apparatus 1 of FIG. 1. However, in the apparatus according to FIG. 2, the hemostasis unit 2, the blood gas unit 3 and the temperature unit 4 are integrated into a single housing 10 (except for a temperature sensor that is not shown in FIG. 2). Preferably, the logic for the hemostasis unit 2, the blood gas unit 3 and the temperature unit 4 are integrated onto the same circuit board or even onto the same chip 11.

Further, the apparatus 1 of FIG. 2 comprises two cartridges 12, 13 for blood samples. Cartridge 12 is used by the hemostasis unit 2 to determine the hemostasis parameter. Cartridge 13 is used by the blood gas unit 3 to determine the blood gas parameter.

If the period of time between taking the blood samples of the patient and determining the hemostasis parameter/blood gas parameter is short, e.g. smaller than approximately 15 minutes, it is preferred to analyze the blood samples as is, i.e. without additives like e.g. heparin, in the cartridges 12, 13. However, if the period of time is substantially longer than 15 minutes, it is preferred to add an inhibitor like heparin to the blood samples immediately after taking the blood sample from the patient. This will prevent the blood from coagulating. Yet, in order to measure hemostasis parameters like clotting time it may be necessary to remove the inhibitor. This can be done by adding an antagonist, e.g. protamin, to the blood sample set up for measuring the hemostasis parameter.

According to the embodiment of FIG. 2, the temperature unit measures not only the temperature of the patient but also the temperature of each blood sample in the cartridges 12, 13.

Rather than having two cartridges 12, 13, only a single cartridge may be used. The hemostasis parameter and blood gas parameter may then be measured in different sectors of the blood sample.

Figure 3:
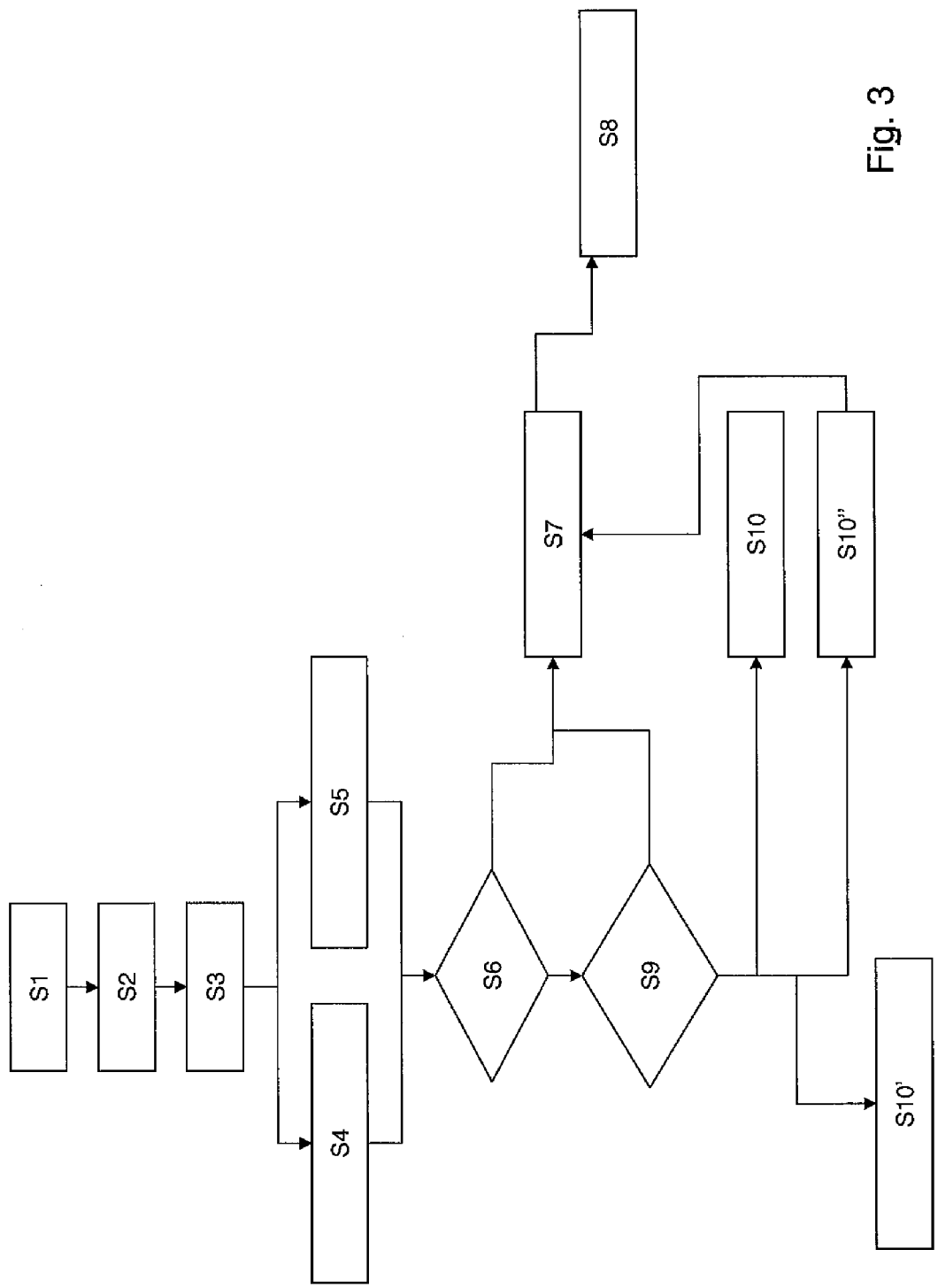
FIG. 3 is a flow chart illustrating a preferred embodiment of a method in accordance with the present invention.

With reference to FIG. 3, a preferred embodiment of a method in accordance with the present invention is explained. The method may be performed by the apparatuses of FIGS. 1 and 2.

Initially, a blood sample is taken from a patient or a blood product (step S1).

The temperature of the blood sample is controlled (step S3) by a suitable heating and/or cooling device which may be part of the apparatus 1. For example, a patient is cooled down for heart surgery. Then, it may be advisable to bring the blood samples temperature to the patient's temperature since the temperature of the blood sample may change once it is taken from the patient, when it is desired to analyze the patient's current situation with regard to coagulation, for example. To this end, the patient's temperature is measured in the foregoing step (step S2). Or, the temperature of the blood sample is brought to normal temperature (37° Celsius) in order to simulate the patient's condition on waking up.

According to a further embodiment, the temperature of the blood sample is not controlled but an expected temperature is provided by the anesthetist, e.g. by entering the same via the temperature unit 6.

Thereafter, a blood gas parameter of the blood sample, e.g. pH, is determined (step S4). Before, parallel to, or after step 4, a hemostasis parameter of the blood sample, e.g. clotting time and/or clot formation time, is determined (step S5).

In step S6, it is determined if the hemostasis parameter is a function of the blood gas parameter. To this end, an interdependence parameter for the blood gas parameter and hemostasis parameter at the measured or expected temperature (temperature parameter) is read from a data storage, which may be part of the apparatus 1. The interdependence parameter may be stored electronically in a table of the following form:

| blood gas parameter | hemostasis parameter | temperature parameter (° Celsius) | interdependence parameter |
|---|---|---|---|
| pH | clot formation time | 30-33 | Yes |
| pH | clot formation time | 36-39 | No |
| pH | clotting time | 30-33 | No |
| pH | clotting time | 36-39 | No |
| partial pressure of oxygen | . . . | | . . . |

Figure 4:
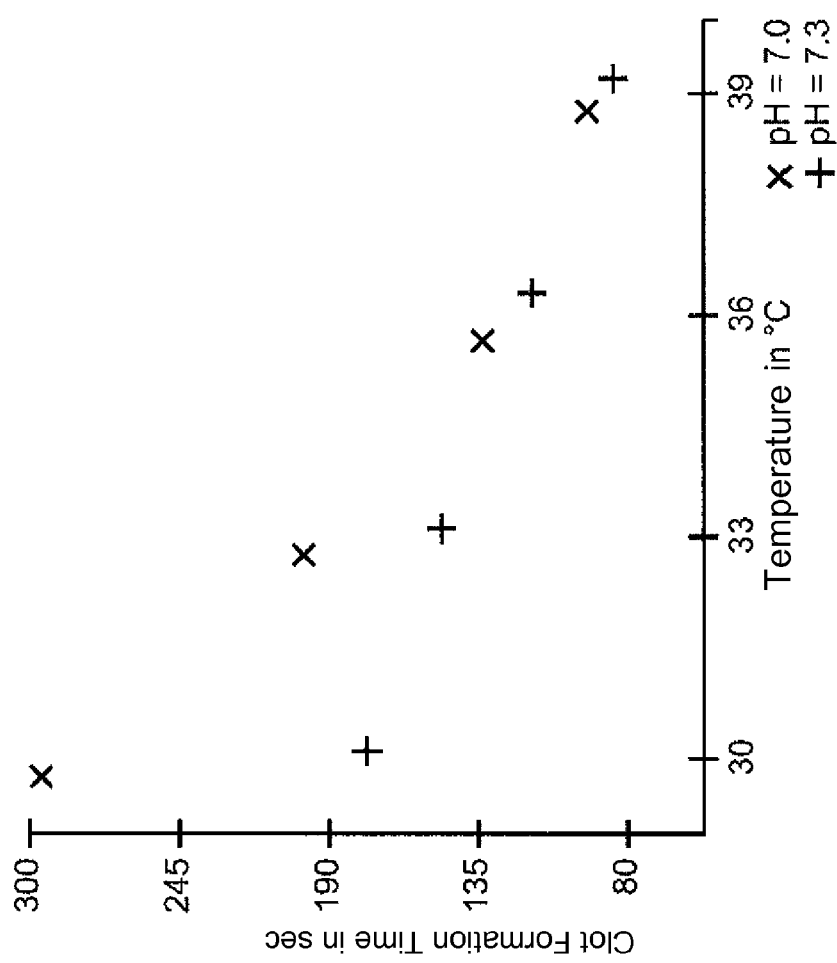
FIG. 4 is a diagram showing clot formation time vs. temperature for two different pH levels.

The interdependence parameter can be determined in experiments up front like the one shown in FIGS. 4 and 5.

FIG. 4 shows the relationship between clot formation time and pH level for different temperatures. FIG. 5 shows the same relationship for clotting time. As can be gathered from FIGS. 4 and 5, there is no substantial interdependence between clotting time/clot formation time and pH levels at a temperature of 36-39° Celsius. However, there is a strong interdependence between clot formation time and pH levels of 7.0-7.3 at a temperature of 30-33° Celsius.

If it is determined that the hemostasis parameter is not a function of the blood gas parameter, then the hemostasis parameter is displayed on a screen to the anesthetist in Step S7. Seeing the hemostasis parameter being displayed, the anesthetist knows that the hemostasis parameter has been determined accurately. He or a further device can now analyze the hemostasis parameter with regard to disorders, e.g. coagulopathy, in step S8.

Step S6 increases efficiency but is optional.

Otherwise, i.e. if the hemostasis parameter is a function of the blood gas parameter, it is determined if the blood gas parameter is allowable. E.g. a pH-level of smaller than 7.0 will not allow for reliable measurements of clotting time. To this end, allowable ranges of the blood gas parameter are read from a data storage, which may be part of the apparatus 1. The allowable ranges may be stored electronically in a table of the following form:

| blood gas parameter | allowable range |
|---|---|
| pH | 7.0 < pH < 7.4 |
| partial pressure of oxygen | . . . |

Of course, the table may also include the temperature parameter.

Hence in step S9, the blood gas parameter is compared to its allowable range. If it is within its allowable range, step 7 follows.

In addition or as an alternative, step 9 may also be performed with respect to the temperature parameter to ensure that the temperature parameter is within its allowable range for a specific hemostasis parameter.

If the blood gas parameter is not within its allowable range, according to one embodiment, the hemostasis parameter will be displayed on the screen accompanied by a warning "pH value out of range" (step S10). It is then up to the anesthetist to adjust the pH-level in the blood sample. In this case, the evaluation parameter is comprised of the hemostasis parameter being displayed/the warning being displayed along with hemostasis parameter.

According to an alternative embodiment, the hemostasis parameter is not displayed on the screen but a warning "pH value out of range" (step S10'). It is then up to the anesthetist to adjust the pH-level in the blood sample. By not displaying the hemostasis parameter, it is ensured that the anesthetist will only continue with step S8 once the hemostasis parameter is correct. In this case, the evaluation parameter is comprised of displaying/not displaying the hemostasis parameter.

If a plurality of hemostasis parameters are being determined, it may be useful to apply step S10' to each hemostasis parameter individually, i.e. only the hemostasis parameters which are incorrect are not being displayed, whereas the correct hemostasis parameters are displayed and can be used by the anesthetist. However, a more simple method could be designed such as to display none of the hemostasis parameters if one of them shows to be incorrect.

According to a further alternative embodiment, the hemostasis parameter is automatically corrected to make up for the blood parameter and/or temperature parameter not being inside its allowable range (Step 10'). This correction may be based on experimental data, stored in formulae and/or in tables on an electronic storage device, which may also be part of the apparatus 1. After correction of the hemostasis, the method continues at step S7. In this case, the evaluation parameter is comprised of the corrected hemostasis parameter being determined and displayed.

The steps S3 and S6-S10" are performed by the evaluation unit 4 of the apparatus 1. Step S4 is performed by the blood gas unit 3 and step S5 by the hemostasis unit 2 of the apparatus 1.

Although the present invention has been described in accordance with preferred embodiments, it is obvious for a person skilled in the art that modifications are possible in all embodiments.

Of course the invention is not limited to be used by anesthetists but can be used by any medical practitioner, in particular.

What is claimed is:

1. An apparatus for determining at least one evaluation parameter of a blood sample, comprising:
   a blood gas analyzer configured to determine at least one blood gas parameter of the blood sample from the group of pH level and partial pressure of oxygen;
   a thromboelastometer configured to determine at least one hemostasis parameter of the blood sample from the group of blood clotting time and blood clot formation time; and
   an evaluation unit coupled to the thromboelastometer via a first data interface, coupled to the blood gas analyzer via a second data interface and configured to determine the at least one evaluation parameter as a function of the blood gas parameter and the hemostasis parameter, the evaluation unit comprising a processor;
   wherein the processor is programmed to determine the at least one evaluation parameter of at least one blood sample by carrying out computer-executable instructions on in a non-transitory computer-readable medium for performing steps comprising:

providing the at least one blood gas parameter;

providing the at least one hemostasis parameter;

providing an interdependence parameter describing an interdependence between the blood gas parameter and the hemostasis parameter; and determining the at least one evaluation parameter as a function of the blood gas parameter and the hemostasis parameter;

wherein determining the evaluation parameter comprises at least one of the following: comparing the blood gas parameter with a blood gas parameter range and/or comparing the blood gas parameter with a blood gas parameter value;

wherein comparing the blood gas parameter with a blood gas parameter range and/or comparing the blood gas parameter with a blood gas parameter value is performed as a function of the interdependence parameter; and wherein the interdependence parameter is provided by reading out a sensor, reading out a data input device and/or reading out a data storage.

2. The apparatus according to claim 1, further comprising a single cartridge for the blood sample.

3. The apparatus according to claim 1, wherein a temperature of the blood gas analyzer and/or the thromboelastometer is controlled as a function of a temperature parameter of the blood sample determined by a thermometer.

\* \* \* \* \*